US009394489B2

(12) United States Patent
Yusuf et al.

(10) Patent No.: US 9,394,489 B2
(45) Date of Patent: *Jul. 19, 2016

(54) METHODS FOR RECOVERING ORGANIC HETEROATOM COMPOUNDS FROM HYDROCARBON FEEDSTOCKS

(71) Applicant: Saudi Arabian Oil Company, Dhahran (SA)

(72) Inventors: Zaki Yusuf, Dhahran (SA); Ahmad D. Hammad, Dhahran (SA); Stamatios Souentie, Dhahran (SA); Bandar Fadhel, Dhahran (SA); Nayif Rasheedi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 14/617,358

(22) Filed: Feb. 9, 2015

(65) Prior Publication Data

US 2015/0166902 A1      Jun. 18, 2015

Related U.S. Application Data

(63) Continuation of application No. 14/107,471, filed on Dec. 16, 2013, now Pat. No. 8,961,780.

(51) Int. Cl.
| | | |
|---|---|---|
| *C10G 21/12* | (2006.01) | |
| *C10G 21/28* | (2006.01) | |
| *C07C 7/10* | (2006.01) | |
| *B01J 3/00* | (2006.01) | |
| *C10G 21/08* | (2006.01) | |
| *B01D 11/04* | (2006.01) | |

(52) U.S. Cl.
CPC ............ *C10G 21/28* (2013.01); *B01D 11/0403* (2013.01); *B01J 3/008* (2013.01); *C07C 7/10* (2013.01); *C10G 21/08* (2013.01); *C10G 2300/202* (2013.01); *C10G 2300/205* (2013.01); *C10G 2300/44* (2013.01)

(58) Field of Classification Search
CPC ........................................................ C10G 1/04
USPC ........................................................ 208/325
See application file for complete search history.

(56) References Cited

U.S. PATENT DOCUMENTS

| | | |
|---|---|---|
| 2,541,458 A | 2/1951 | Berg |
| 3,231,487 A | 1/1966 | Nettles |
| 3,649,500 A | 3/1972 | Watson et al. |
| 3,969,196 A | 7/1976 | Zosel |
| 4,098,692 A | 7/1978 | Baker |
| 4,746,420 A | 5/1988 | Darian et al. |
| 4,778,591 A | 10/1988 | Reynolds |
| 4,964,995 A | 10/1990 | Chum et al. |
| 5,120,900 A | 6/1992 | Chen et al. |
| 5,143,594 A | 9/1992 | Stephenson et al. |
| 5,329,045 A | 7/1994 | Dedieu et al. |
| 6,183,521 B1 | 2/2001 | Lin et al. |
| 6,187,175 B1 | 2/2001 | Blum et al. |
| 6,248,797 B1 | 6/2001 | Dias et al. |
| 6,566,410 B1 | 5/2003 | Zaki et al. |
| 7,622,035 B2 | 11/2009 | Zaki et al. |
| 8,257,579 B2 | 9/2012 | Barrero et al. |
| 8,431,358 B2 | 4/2013 | Sadowski et al. |
| 8,574,426 B2 | 11/2013 | Mezza et al. |
| 2004/0065353 A1* | 4/2004 | Tunnicliffe ........ B01D 11/0203 134/26 |
| 2011/0049016 A1 | 3/2011 | McGrady et al. |
| 2011/0098507 A1 | 4/2011 | Cohrs et al. |
| 2012/0279902 A1 | 11/2012 | McGrady et al. |

FOREIGN PATENT DOCUMENTS

| | | | |
|---|---|---|---|
| CA | 949910 A | 6/1974 | |
| CA | 1023677 A | 1/1978 | |
| CN | 87105863 A | 3/1988 | |
| CN | 103214332 A | 7/2013 | |
| DE | 10 2007 060 651 B3 | 6/2009 | |
| EP | 0922746 A2 * | 11/1998 | ............. C10G 32/02 |
| EP | 0 922 746 A2 | 6/1999 | |
| EP | 1177269 | 2/2002 | |

(Continued)

OTHER PUBLICATIONS

Bauserman et al. Ind. Eng. Chem. Res. 2008, 47, 2867-2875 0922746.*
Hioyshi et al. Journal of Supercritical fluids 2010, 55, 122-127.*
International Search Report and Written Opinion dated Aug. 6, 2015 pertaining to International Application No. PCT/US2015/031327.
Nael N. Zaki, Ruben G. Carbonell, Peter K. Kilpatrick; A Novel Process for Demulsification of Water-in-Crude Oil Emulsions by Dense Carbon Dioxide; Ind. Eng. Chem. Res. 2003, 42, pp. 6661-6672.
Xiaoli Yang, Vincent J. Verruto, Peter K. Kilpatrick; Dynamic Asphaltene-Resin Exchange at the Oil/Water Interface: Time-Dependent W/O Emulsion Stability for Asphaltene/Resin Model Oils; Energy & Fuels 2007, 21, pp. 1343-1349.

(Continued)

*Primary Examiner* — Nizal Chandrakumar
(74) *Attorney, Agent, or Firm* — Dinsmore & Shohl LLP

(57) ABSTRACT

Methods for recovering organic heteroatom compounds from a hydrocarbon feedstock include feeding into a contactor a hydrocarbon feedstock and an aqueous solvent to form an extraction mixture of the aqueous solvent with the hydrocarbon feedstock. The hydrocarbon feedstock includes a hydrocarbon and an organic heteroatom compound. The aqueous solvent includes an ionic liquid formed from pressurized carbon dioxide and water. A pressure and temperature of the extraction mixture may be established that together tune the aqueous solvent to selectively form a solvent complex with the at least one organic heteroatom compound. Then, the solvent complex is extracted to a recovery vessel from the extraction mixture in the contactor. By adjustment of a recovery temperature of the recovery vessel, a recovery pressure of the recovery vessel, or both, the solvent complex decomposes into carbon dioxide and the organic heteroatom compound. The organic heteroatom compound is then recovered from the recovery vessel.

28 Claims, 4 Drawing Sheets

(56) References Cited

FOREIGN PATENT DOCUMENTS

| | | |
|---|---|---|
| EP | 2164930 A1 | 3/2010 |
| EP | 2 338 955 A1 | 6/2011 |
| EP | 2542651 A1 | 1/2013 |
| EP | 2571961 A2 | 3/2013 |
| WO | 0056842 A1 | 2/2000 |
| WO | 00/76617 A1 | 12/2000 |
| WO | 02066137 A1 | 8/2002 |
| WO | 2008154576 A1 | 12/2008 |
| WO | 2010/148204 A2 | 12/2010 |
| WO | 2011081601 A1 | 7/2011 |
| WO | 2011106891 A1 | 9/2011 |
| WO | 2011145086 A2 | 11/2011 |
| WO | 2013089866 A1 | 6/2013 |
| WO | 2013121219 A1 | 8/2013 |

OTHER PUBLICATIONS

Xuemei Chu, Yufeng Hu, Jiguang Li, Qianqing Liang; Yansheng Liu, Xianming Zhang, Xiaoming Peng, Wenjia Yue; Desulfurization of Diesel Fuel by Extraction with [BF4]-based Ionic Liquids; Chinese Journal of Chemical Engineering, 16(6); 2008; pp. 881-884.

Jian-Long Wang, Di-Shun Zhao, Er-Peng Zhou, Zhi Dong; Desulfurization of gasoline by extraction with N-alkyl-pyridinium-based ionic liquids; Journal of Fuel Chemistry and Technology; vol. 35; Issue 3; Jun. 2007; pp. 293-296.

Luisa Alonso, Alberto Arce, Maria Francisco, Ana Soto; Solvent extraction of thiophen from n-alkanes (C7, C12, and C16) using the ionic liquid [C8mim][BF4]; ScienceDirect The Journal of Chemical Thermodynamics 40; 2008; pp. 966-972.

Borja Rodriquez-Cabo, Maria Francisco, Ana Soto, Alberto Arce; Hexyl dimethylpyridinium ionic liquids for desulfurization of fuels. Effect of the position of the alkyl side chains; ScienceDirect Fluid Phase Equlibria 314; 2012, pp. 107-112.

Maria Francisco, Alberto Arce, Ana Soto; Ionic liquids on desulfurization of fuel oils; ScienceDirect Fluid Phase Equilibria 294; 2010; pp. 39-48.

Cun Zhang, Feng Wang, Xiao-Yu Pan, Xiao-Qin Liu; Study of extraction-oxidation desulfurization of model oil by acidic ionic liquid; ScienceDirect Journal of Fuel Chemistry and Technology; vol. 39; Issue 9; Sep. 2011; pp. 689-693.

Fa-Tang Li, Cheng-Guang Kou; Zhi-Min Sun; Ying-Juan Hao; Rui-Hong Liu; Di-Shun Zhao; Deep extractive and oxidative desulfurization of dibenzothiophene with C5H9NO.SnCl2 coordinated ionic liquid; SciVerse ScienceDirect Journal of Hazardous Materials 205-206; 2012; pp. 164-170.

Josef Planeta, Pavel Karasek, Michal Roth; Distribution of sulfur-containing aromatics between [hmim] [Tf2N] and supercritical CO2: a case study for deep desulfurization of oil refinery streams by extraction with ionic liquids; Green Chemistry; 2006; 8; pp. 70-77.

Jie Liu, Xuewen Sun, Dongbao Fu, Suoqi Zhao; Phase equilibria for separation of high boiling point organics from ionic liquids by supercritical CO2 or C3H8; Chemical Engineering Journal 147; 2009; pp. 63-70.

Norihito Hiyoshi, Yuka Murakami, Aritomo Yamaguchi, Osamu Sato, Chandrashekhar V. Rode, Masayuki Shirai; Purification of hydrocarbons from aromatic sulfur compounds by supercritical carbon dioxide extraction; The Journal of Supercritical Fluids 55; 2010; pp. 122-127.

International Search Report and Written Opinion dated Mar. 16, 2015 pertaining to International Patent Application No. PCT/US2014/068048.

International Search Report and Written Opinion dated Mar. 18, 2015 pertaining to International Patent Application No. PCT/US2014/068047.

Notice of Allowance dated Jun. 30, 2015 pertaining to U.S. Appl. No. 14/143,711.

* cited by examiner

METHODS FOR RECOVERING ORGANIC HETEROATOM COMPOUNDS FROM HYDROCARBON FEEDSTOCKS

CROSS REFERENCE TO RELATED APPLICATIONS

This application is a continuation of currently pending U.S. patent application Ser. No. 14/107,471 filed Dec. 16, 2013.

BACKGROUND

1. Field

The present specification generally relates to recovery of organic heteroatom compounds from hydrocarbon feedstocks. More particularly, the present specification is directed to methods for separating heteroatom compounds from hydrocarbons using a tunable/switchable/reversible solvent.

2. Technical Background

Organic heteroatom-containing compounds such as sulfur compounds, nitrogen compounds, and organometallic compounds, have numerous uses and applications as starting materials or feedstocks in technologies such as solar energy harvesting, organic photovoltaic and solar cell manufacturing, organic LED manufacturing, organic thin-film transistor manufacturing, and pharmaceutical manufacturing. These compounds have high abundance in crude oils, particularly in heavy crude oils, but are typically removed from the crude oils by hydrotreatment (HDT) or oxidative desulfurization or denitrogenation to meet environmental regulations with regard to fuel sulfur and nitrogen content. During the HDT, oxidative desulfurization, or denitrogenation processes, the organic heteroatom-containing compounds typically undergo molecular transformations and not retain their molecular structure, thereby rendering them useless to further applications.

Accordingly, systems and methods that enable recovery of organic heteroatom compounds from hydrocarbons are desirable.

SUMMARY

According to some embodiments, methods for recovering organic heteroatom compounds from a hydrocarbon feedstock may include feeding a hydrocarbon feedstock into a contactor, the hydrocarbon feedstock comprising at least one hydrocarbon and at least one organic heteroatom compound. An aqueous solvent may be fed into the contactor to form an extraction mixture of the aqueous solvent with the hydrocarbon feedstock, the aqueous solvent comprising an ionic liquid formed from pressurized carbon dioxide and water. A contactor pressure and a contactor temperature of the extraction mixture in the contactor may be established that together tune the aqueous solvent to selectively form a solvent-organic complex with the at least one organic heteroatom compound. Then, the solvent-organic complex may be extracted to a recovery vessel from the extraction mixture in the contactor. By adjustment of a recovery temperature of the recovery vessel, a recovery pressure of the recovery vessel, or both, the solvent-organic complex may be decomposed/dissociated in the recovery vessel into carbon dioxide, water molecule and the at least one organic heteroatom compound. Then, the at least one organic heteroatom compound may be recovered from the recovery vessel.

According to other embodiments, methods for recovering organic heteroatom compounds from a hydrocarbon feedstock may include feeding a hydrocarbon feedstock into a contactor. The hydrocarbon feedstock may include crude oil or a crude oil fraction and at least one organic heteroatom compound. The organic heteroatom may be chosen from nitrogen-containing heterocyclic compounds, sulfur-containing heterocyclic compounds, porphyrins, organometallic compounds, and combinations thereof. An aqueous solvent may be fed into the contactor to form an extraction mixture of the aqueous solvent with the hydrocarbon feedstock. The aqueous solvent may include an ionic liquid formed from pressurized carbon dioxide and water. A contactor pressure and a contactor temperature of the extraction mixture may be established in the contactor that together tune the aqueous solvent to selectively form a solvent complex with the at least one organic heteroatom compound. Then, the solvent complex may be extracted to a recovery vessel from the extraction mixture in the contactor. The solvent complex in the recovery vessel may be depressurized to decompose/dissociate the solvent complex into carbon dioxide and the at least one organic heteroatom compound. Then, the at least one organic heteroatom compound may be recovered from the recovery vessel.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
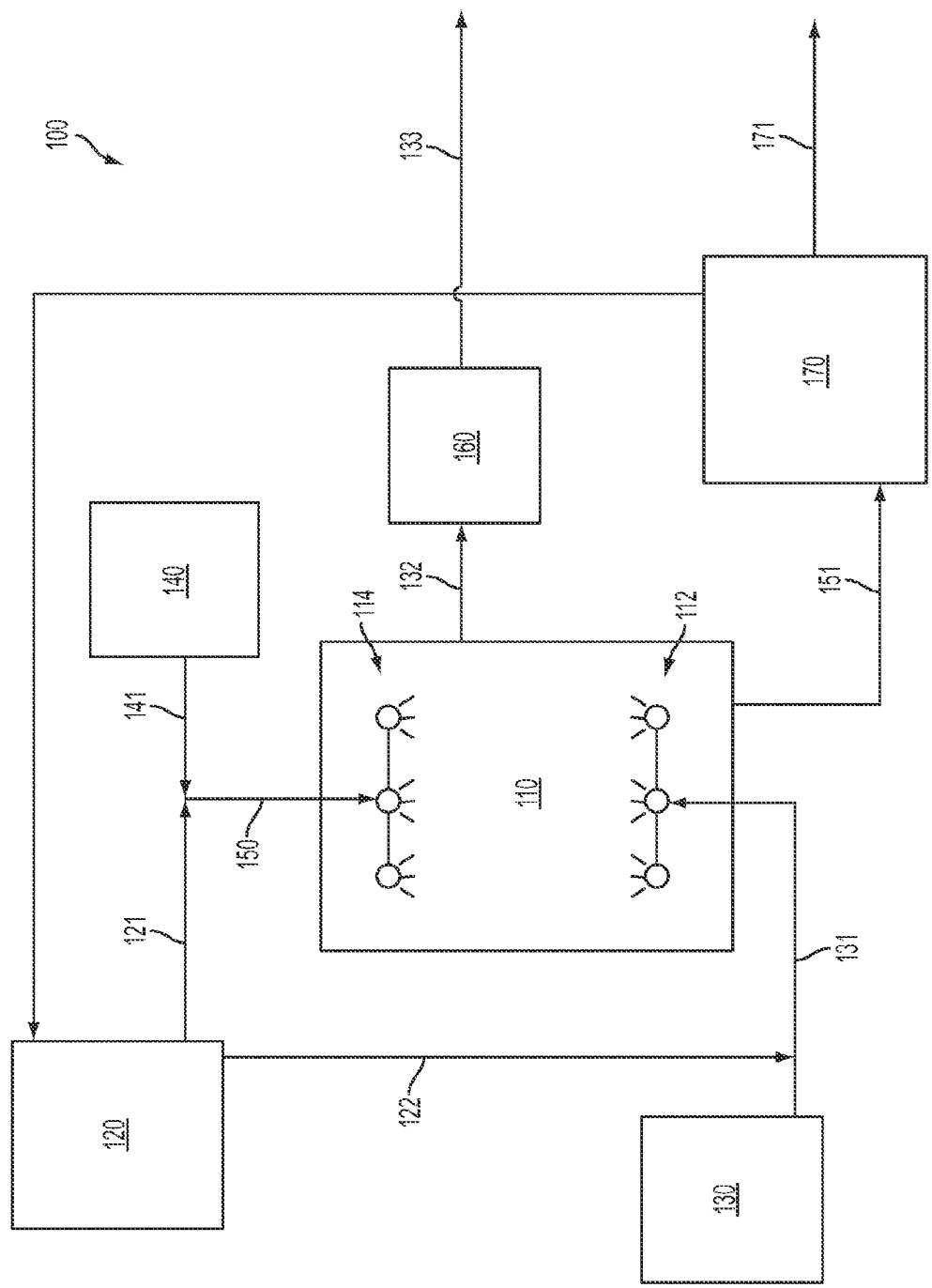
FIG. 1 schematically depicts components of a system for separating organic heteroatom compounds from a hydrocarbon feedstock according to embodiments described herein.

Removing refractory organic heteroatom compounds, such as, for example, sulfur compounds, nitrogen compounds, and organometallic compounds, from hydrocarbon feedstocks, such as, for example, crude oil or crude oil fractions, can be a difficult process because of the stubborn behavior of these compounds to transform during HDT, e.g., desulfurization and/or denitrogenation processes. Therefore, separating the organic heteroatom compounds from the hydrocarbon feedstocks can be both energy and cost prohibitive. In addition, using desulfurization and/or denitrogenation it can be difficult to control side reactions that can impede the separation process or introduce further impurities into the hydrocarbon feedstocks.

Some embodiments herein include methods for separating and recovering organic heteroatom compounds from a hydrocarbon feedstock using a reversible/switchable/tunable solvent (hereinafter referred to as "tunable solvent"). As used herein, the term "organic heteroatom compounds" refers to organic compounds that contain at least one atom other than carbon and hydrogen. Examples of organic heteroatom compounds include organosulfur compounds such as sulfur-containing heterocyclic compounds, organonitrogen compounds such as nitrogen-containing heterocyclic compounds, and organometallic compounds such as porphyrins. In some embodiments, the organic heteroatom compounds may be natural impurities found in a hydrocarbon feedstock such as crude oil or a crude oil fraction, for example. The tunable solvent allows the organic heteroatom compounds to maintain their physical and chemical properties upon separation from the hydrocarbon feedstock. In some embodiments, the tunable solvent may be an ionic liquid, a gas expanded ionic liquid, or another solvent that selectively attracts the organic heteroatom compounds. The tunable solvent may form a reversible complex with the organic heteroatom compounds. In some embodiments, various properties of the tunable solvent can be controlled so that the tunable solvent becomes more ionic or less ionic in nature and, thus, may be selectively attracted to or selectively form reversible complexes with one or more chosen organic heteroatom compounds.

Different hydrocarbon feedstocks, particularly those derived from crude oil or crude oil fractions, can contain different types of organic heteroatom compounds. By adjusting the solubility parameters of the target organic heteroatom compound, such as, for example, exploiting the polarity of any target organic heteroatom compound, impurities in the hydrocarbon feedstock may be selectively separated from the hydrocarbon feedstocks using the tunable solvent. In some embodiments, the tunable solvent may be modified by adjusting the pressure, temperature, and/or pH of the solvent system so that the target organic heteroatom compound is maintained as a solute in the solvent system. Once the organic heteroatom compound is solvated, further adjustment of the pressure, temperature, and/or pH of the solvent system may reverse the solvation, whereby the organic heteroatom compound can be easily recovered as an aggregate, a precipitate, or the like.

In some embodiments, the tunable solvent may be modified by, for example, adjusting the pressure of the solvent system so that the solvent is tuned to attract or complex with a target organic heteroatom compound that has a certain polarity. By using such a selective solvent, interference from impurities that are not the target organic heteroatom compound may be less likely than in other separation processes. For example, separation processes that separate impurities based on, for example, the boiling point and condensation point of impurities may be likely to separate impurities other than the target organic heteroatom compound, particularly ones that have a similar boiling point as the target organic heteroatom compound. In contrast, tunable solvents according to embodiments herein may be precisely tuned so that they selectively separate only the target organic heteroatom compound. In other embodiments, the tunable solvent may be modified, such as by adjusting the pressure of the solvent system, so that the tunable solvent separates the organic heteroatom compounds from the hydrocarbons. For example, in some embodiments, the tunable solvent may be modified to attract or complex with the most polar organic heteroatom compound as a solute in the solvent system. In other embodiments, the tunable solvent may be modified to attract organic heteroatom compounds having even weak polarity, such as, for example, weak dipole moments. In addition to pressure, temperature may be used, in embodiments, to modify the equilibrium of the solvent-organic system. For example, temperature may be used to affect the solubility of the of the organic heterocyclic molecules. Increased solubility of the organic heterocyclic molecules may increase the extraction and selectivity of the solvent-organic system and, thereby, temperature may be used to fine-tune the tunable solvent.

In the methods for recovering organic heteroatom compounds from a hydrocarbon feedstock according to some embodiments, the hydrocarbon feedstock, such as, for example, crude oil or crude oil fraction, may be contacted with a tunable solvent that is capable of being modified, or tuned, to attract one or more organic heteroatom compounds into the solvent system as a solute. Contacting of the hydrocarbon feedstock with the tunable solvent may include feeding the hydrocarbon feedstock into a contactor, and feeding the aqueous solvent into the contactor to form an extraction mixture of the aqueous solvent with the hydrocarbon feedstock. The tunable solvent may be formed from pressurized carbon dioxide, water, and optional modifiers. Changes in pressure of the solvent system can be used to tune the tunable solvent to attract specific organic heteroatom compounds into the solvent system as a solute. Accordingly, the methods may include establishing a contactor pressure and a contactor temperature of the extraction mixture in the contactor that together tune the aqueous solvent to selectively form a solvent complex with the at least one organic heteroatom compound.

In some embodiments, the aqueous solvent includes supercritical carbon dioxide. In some embodiments, the aqueous solvent includes subcritical carbon dioxide. In other embodiments, the aqueous solvent comprises both supercritical and subcritical carbon dioxide.

Without intent to be bound by theory, characteristics of the solvent system applicable to embodiments of methods for recovering organic heteroatom compounds will now be described using the equations and description below. In the following equations, gaseous carbon dioxide is denoted by "$CO_2$ (g)" and may have a partial pressure $P_{CO_2}$, dissolved carbon dioxide is denoted by "$CO_2$ (aq)", and dissolved carbonic acid is denoted by "$H_2CO_3$." In some embodiments, dissolved carbon dioxide may account for greater than or equal to about 90.0% of the dissolved components, such as greater than or equal to about 95.0% of the dissolved components. In other embodiments, dissolved carbon dioxide may account for greater than or equal to about 97.0% of the dissolved components, such as greater than or equal to about 99.0% of the dissolved components. In some embodiments, dissolved carbon dioxide may account for 99.85% of the dissolved components, and dissolved carbonic acid may account for 0.15% of the dissolved components. The dissolved components in the solvent system may be denoted as $H_2CO_3{}^*$, as shown in equation (A) below.

$$[H_2CO_3{}^*(aq)] = [H_2CO_3(aq)] + [CO_2] \tag{A}$$

With respect to pressure, gaseous carbon dioxide may be in equilibrium with dissolved carbonic acid in accordance with formulas (B) and (C) below.

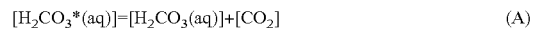
$$CO_2(g) + H_2O(aq) \longleftrightarrow H_2CO_3{}^*(aq) \tag{B}$$

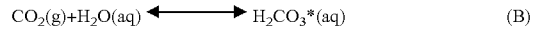
$$H_2CO_3{}^*(aq) \longleftrightarrow H^+(aq) + HCO_3{}^-(aq) \tag{C}$$

Thus, the relationship between dissolved carbon dioxide and dissolved carbonic acid may have the relationship shown in equation (D).

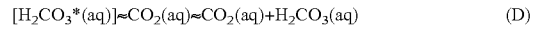
$$[H_2CO_3{}^*(aq)] \approx CO_2(aq) \approx CO_2(aq) + H_2CO_3(aq) \tag{D}$$

Gaseous carbon dioxide may be in equilibrium with the carbon in an aqueous phase in the contactor according to Henry's law, as denoted in equation (E), where Henry's law constant is denoted as $k_H$ (mole/(kg·atm)).

$$CO_2(aq) = P_{CO_2}/k_H \qquad (E)$$

Thus, the solubility of aqueous phase carbon dioxide may increase with respect to increasing pressure of the solvent system employed in the methods according to some embodiments. In addition, the solubility of gaseous carbon dioxide in water increases as the temperature of the solvent system decreases. However, to maintain supercritical behavior of carbon dioxide in the solvent system, according to embodiments, the temperature and the pressure of the solvent system may be maintained above the critical temperature and pressure of carbon dioxide. As a result, the combined effect of the carbon dioxide and water in the tunable solvent achieves unique properties that allow the solvent to be used to attract or complex with organic heteroatom compounds from hydrocarbon feedstocks into the solvent system as a solute.

Properties of the tunable solvent system included in various embodiments will be described in equations below, where a(j) is the activity of the involved species "j."

$$K_1 = \{a(H^+)a(HCO_3^-)\}/a(H_2CO_3) \qquad (F)$$

Using commonly known definitions of pH and pK, equation (F) may be rewritten as equation (G):

$$pK_1 = pH + \log\{[H_2CO_3^*]/[HCO_3^-]\} - \log(\gamma_a) \qquad (G)$$

In equation (G), $\gamma_a$ is the activity coefficient of $HCO_3^-$. The activity coefficient of a neutral species may be assumed to be unity.

As shown by the above equations, the carbon dioxide in the solvent system according to embodiments herein may play multiple roles in the separation process. Supercritical carbon dioxide may diffuse through the hydrocarbon feedstock because it has good diffusivity and lower viscosity than other solvents, which allows the carbon dioxide to better initiate the mass transfer that attracts the organic heteroatom compounds into the solvent system as a solute. For example, in embodiments, the polar nature of refractory sulfur compounds, nitrogen compounds, and organometallic compounds may bring the organics into the reversible aqueous phase of the solvent. For example, the polar characteristics of the organic heteroatom compounds may be attracted by the $HCO_3^-$ in the $H_2CO_3^*$ (aq) phase.

In some embodiments, the temperature of the solvent system, the pressure of the solvent system, or both, may be adjusted to tune the solvent system to contain more or fewer ions, such as, for example, $HCO_3^-$, thereby making the solvent system more or less attractive to ionic refractory components or to tune the solvent system's ability to form complexes between the tunable solvent and the organic heteroatom compound. To remove target refractory components, such as, for example, target organic sulfur compounds, target organic nitrogen compounds, target organometallic compounds, or combinations thereof, properties such as boiling point, as well as the chemical structures of the of the target organic heteroatom compounds may affect temperature and pressure parameters that result in selectivity of the solvent system. Various organic sulfur compounds, organic nitrogen compounds, and organometallic compounds are shown in TABLE 1 as examples of the organic heteroatom compounds that may be removed from hydrocarbon feedstocks in various embodiments. It should be understood that the compounds listed below are only exemplary in nature and are not intended to be an exhaustive list of all organic heteroatom compounds that may be removed according to embodiments of this disclosure.

TABLE 1

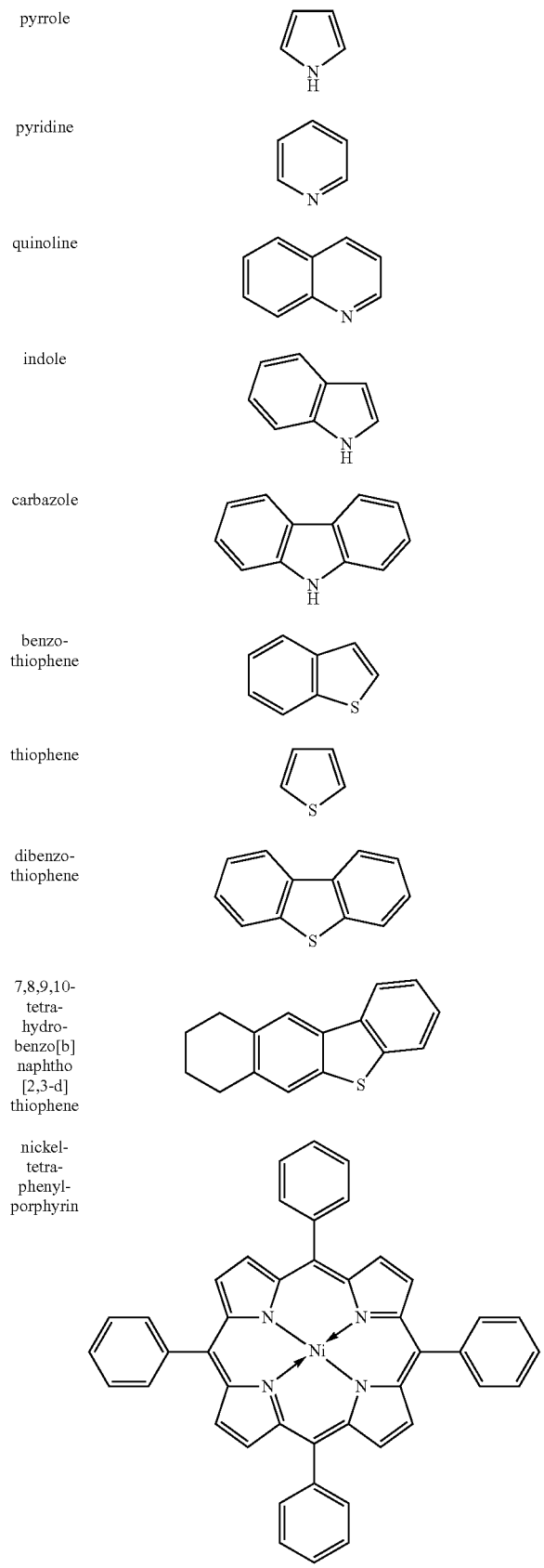

pyrrole pyridine quinoline indole carbazole benzo-thiophene thiophene dibenzo-thiophene 7,8,9,10-tetra-hydro-benzo[b]naphtho[2,3-d]thiophene nickel-tetra-phenyl-porphyrin TABLE 1-continued

| vanadyl-tetra-phenyl-porphyrin | 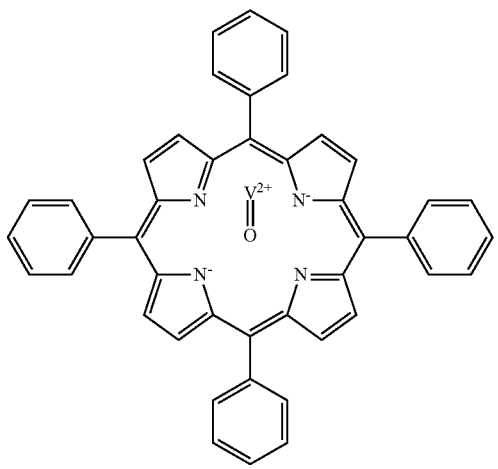 |
|---|---|

As should be evident from the organic heteroatom compounds in TABLE 1, the compounds that may be removed from hydrocarbon feedstocks according to various embodiments may have varieties of chemical structures. Thus, the compounds that are to be removed from the hydrocarbon feedstocks will have an impact and can determine the appropriate amount of solvent tuning required, such as, for example, adjustments of the pressure and/or temperature of the solvent system. Additionally, in embodiments, the selection of a tunable solvent for the separation of a specific organic heteroatom compound from hydrocarbons may impact the mass transfer of the organic heteroatom compounds from a hydrocarbon phase to a solvent phase that result from phase separation of the extraction mixture.

Tunable solvents and organic heteroatom compounds to be removed from hydrocarbons, such as, for example, crude oil or crude oil fractions, according to embodiments of this disclosure have been described above. Below embodiments of methods and systems for using tunable solvents to separate organic heteroatom compounds are provided. It should be understood that the methods and systems described below are exemplary only and other methods and systems for separating organic heteroatom compounds from hydrocarbons using a tunable solvent are within the scope of this disclosure.

A single stream or a series of streams of tunable solvents may be used for selectively separating organic heteroatom compounds, such as, for example, organic sulfur compounds, organic nitrogen compounds, and/or organometallic compounds, from hydrocarbons. In embodiments, the separation may proceed by running the tunable solvent and the hydrocarbons in a series of cross-current or counter-current contactors, such as, for examples, packed bed contactors, fluidized bed contactors, and baffled contactors.

Referring to FIG. 1, a hydrocarbon feedstock 131, such as crude oil, may be dispersed from a hydrocarbon storage unit 130 into the bottom of contactor 110, such as by bottom spray nozzles 112. Similarly, a tunable solvent 150 may be formed by mixing carbon dioxide 121 from a carbon dioxide storage unit 120 and water 141 from a water storage unit 140. The tunable solvent 150 may be dispersed into the top of the contactor 100, such as by top spray nozzles 114. Droplets and sprays of the hydrocarbon 131 may flow upward, such as by spray propulsion and by filling the bottom of the contactor 110 with the hydrocarbon 131. Droplets and sprays of the tunable solvent 150 may flow downward in the contactor 110, such as by spray propulsion and gravitational forces. Further, in embodiments, the hydrocarbon 131 and the tunable solvent 150 may be selected such that the density of the tunable solvent 150 is greater than the density of the hydrocarbon 131. This difference in density may cause the tunable solvent 150 to contact the hydrocarbon 131 and traverse through the hydrocarbon phase. Thus, in embodiments, the hydrocarbon 131 and the tunable solvent 151 proceed in counter-flow contact, thereby increasing residence time of the contact between the hydrocarbon 131 and the tunable solvent 150.

In some embodiments, the hydrocarbon 131 may optionally be premixed with supercritical carbon dioxide 122 before the hydrocarbon 131 is introduced into the contactor 110 to initiate separation of the target organic heteroatom compounds from the hydrocarbon 131 before it is fed into the contactor 110. For example, supercritical carbon dioxide may be transmitted from the carbon dioxide storage unit 120 into the hydrocarbon 131.

In some embodiments, droplets of both the hydrocarbon 131 and the tunable solvent 150 may coalesce to form separate homogeneous phases at their respective outlets of the contactor 110 (i.e., the bottom of the contactor 110 for the tunable solvent 150 and the top of the contactor 110 for the hydrocarbon 131). In embodiments where the hydrocarbon 131 is more dense than the tunable solvent 150, the flow of these components into the contactor may be reversed (i.e., the denser hydrocarbon 131 may be introduced into the top of the contactor 110, and the tunable solvent 150 may be introduced into the bottom of the contactor 110). During contact between the hydrocarbon 131 and the tunable solvent 150, organic heteroatom compounds may be attracted into the solvent phase of the tunable solvent 150 as solutes, for example, by forming complexes with the tunable solvent. Thus, after the hydrocarbon 131 and the tunable solvent 150 interact for a period of time, lean hydrocarbon 132 may be extracted from the middle of the contactor 110. The tunable solvent 151, which is rich with organic heteroatom compounds, may be removed from the bottom of the contactor 110.

As discussed above, in embodiments, the pressure and/or temperature within the contactor may be modified to tune the solvent to have ions that attract polar components in the hydrocarbon feedstock. Target organic heteroatom compounds, such as, for example, organic sulfur compounds, organic nitrogen compounds, and organometallic compounds naturally have polarities in the molecular structures. For example, dibenzothiophene, shown in TABLE 1 above, has a sulfur atom that is more electropositive than its other, bonded carbon atoms. Particularly, the delocalized electrons of dibenzothiophene may be drawn inside of its ring structure and, thus, the sulfur atoms' outer shell may also be drawn inside toward the electrons. As a result, the sulfur atom attached to the rings becomes electropositive and provides the dibenzothiophene with polar properties.

Because various organic heteroatom compounds have polarities, such as the above-described dibenzothiophene, they can be separated from the hydrocarbon phase into the aqueous phase of the solvent by the $HCO_3^-$ ions by forming a temporary complex between the polar organic heteroatom compound and the $HCO_3^-$ ion. For example, a temporary complex that is formed between dibenzothiophene and $HCO_3^-$ is shown below:

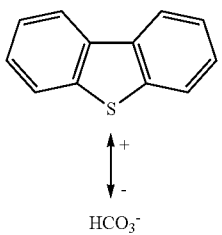 [SMILES: c1ccc2c(c1)sc1ccccc12 ; "HCO3-"]

Organic heteroatom compounds containing nitrogen may also have polar behavior. However, unlike organic sulfur compounds, $HCO_3^-$ or $H^+$ may attract the organic nitrogen compounds because, in certain compounds, the nitrogen bond may have a positive or negative polarity. For example, in carbazole, the N—H bond may take on a positive or negative polarity and, thus, the following complexes may be formed between the tunable solvent and carbazole:

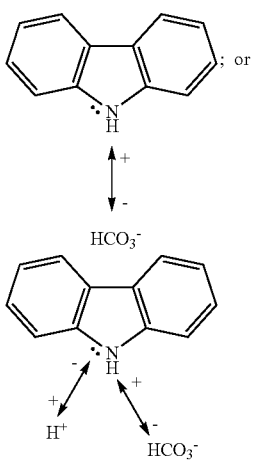

The above reaction mechanisms are exemplary only and are not intended to limit the scope of any embodiment herein. Similar reaction mechanism may occur with respect separation other organic heteroatom compounds, such as, for example, any of the compounds in TABLE 1.

Figure 2:
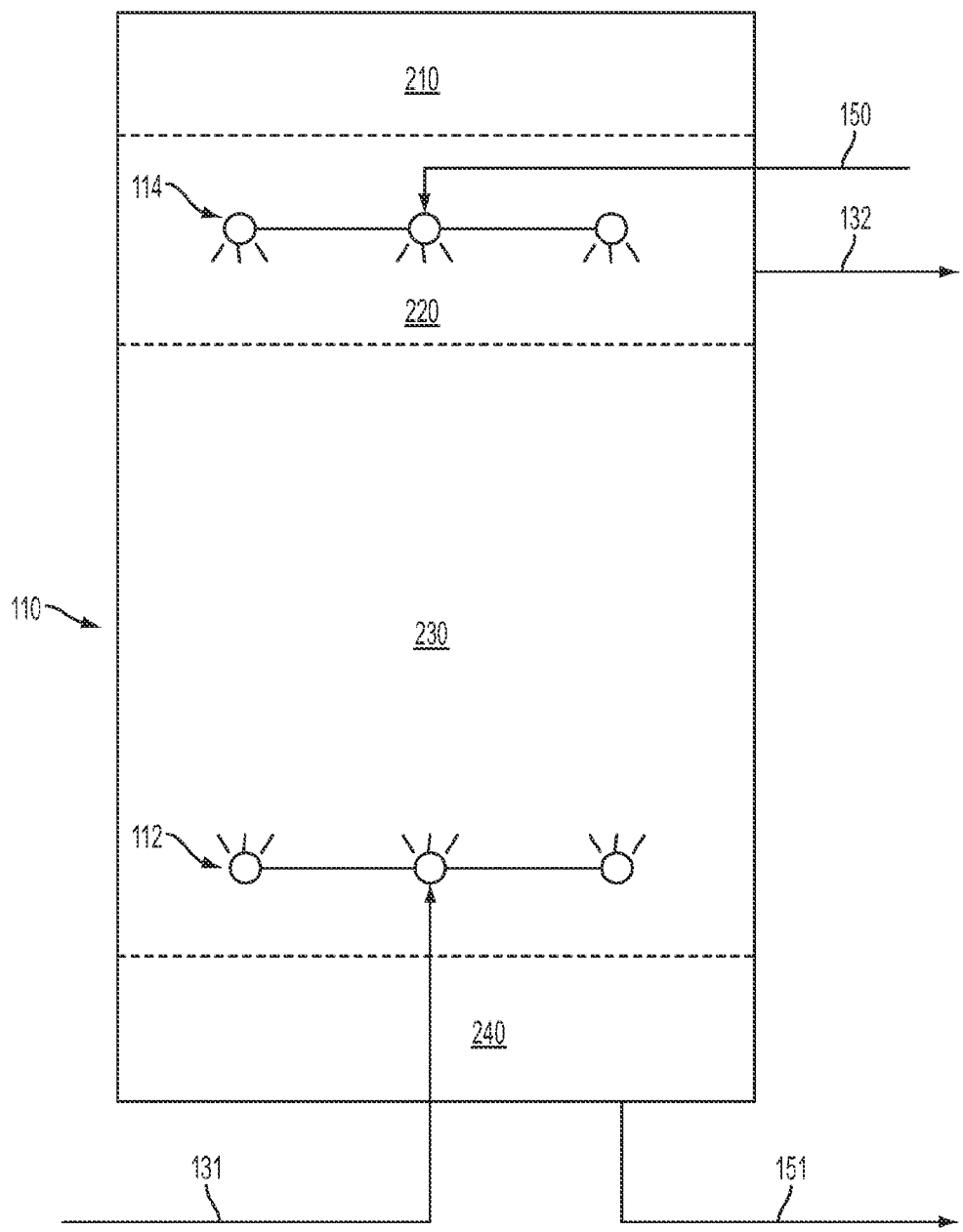
FIG. 2 schematically depicts phases within a contactor according to embodiments described herein.

Further explanation of the extraction mechanism according to embodiments may be made with reference to FIG. 2, which shows the phases in contactor 110 during the reaction between the tunable solvent and the hydrocarbon. In FIG. 2, the fluids in the contactor 110 are divided into four phase regions 210, 220, 230, and 240. Each phase region is separated from adjacent phase region(s) by a phase boundary (represented by dotted lines). According to some embodiments, the top of the contactor 110 may comprise phase 210 that includes supercritical and subcritical carbon dioxide. Below phase 210 is phase 220 that may include lean hydrocarbon and carbon dioxide. In embodiments, the lean hydrocarbon 132 extracted from the contactor 110 may be extracted from phase 220. Below phase 220 is phase 230 that includes a mixture of aqueous carbon dioxide, water, hydrogen ions, carbonic acid, hydrocarbon, and supercritical carbon dioxide. The tunable solvent 150 and the hydrocarbon 131 are introduced into the contactor 110 in phase 220, such as by spraying through spray nozzles 112 and 114. At the bottom of the contactor is phase 240, which may comprise aqueous carbon dioxide, hydrogen ions, water, carbonic acid, and solute rich solvent. The solute rich solvent 151 that is extracted from the contactor may be extracted from phase 240.

Figure 3:
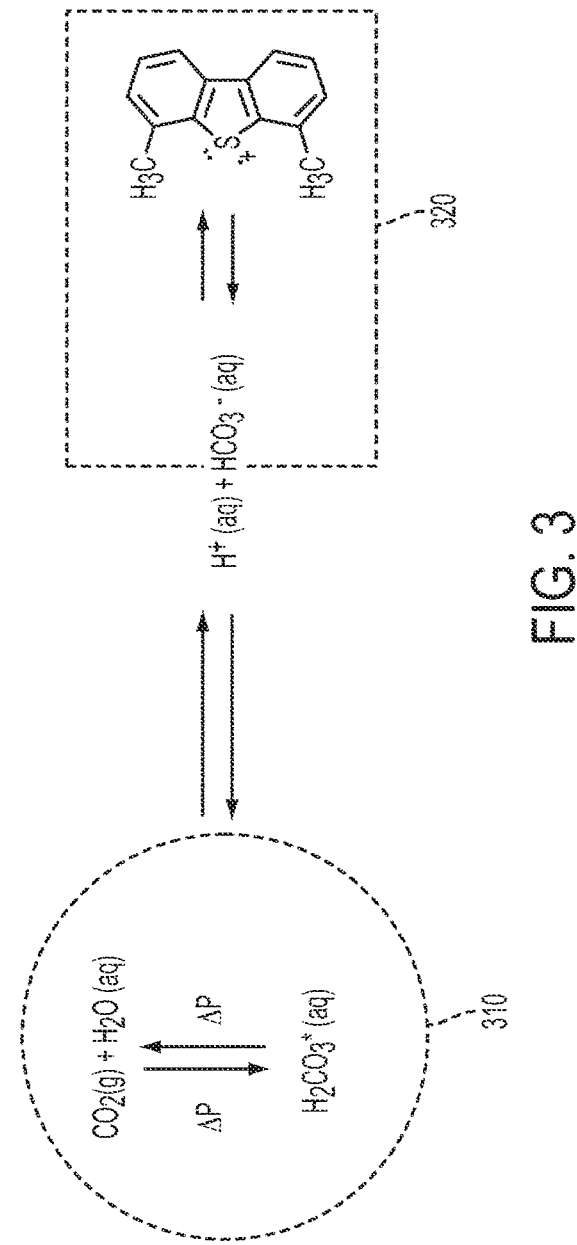
FIG. 3 depicts formation of complexes between organic heteroatom compounds and the solvent according to embodiments described herein.

Using the phases in the contactor 110, such as the phases shown in FIG. 2, the effect of pressure on the solvent system within the contactor 110 may be understood referring to equation (C) above. For example, complexes between organic heteroatom compounds and the solvent, such as the complexes shown above, may be driven by pressure increases in the solvent system. One example of how pressure drives complexes between organic heteroatom compounds and the solvent is shown in FIG. 3, which is exemplary only and does not limit the scope of any embodiment. FIG. 3 shows the formation of $H_2CO_3^*$ (aq), $H^+$ (aq), and $HCO_3^-$ (aq) is promoted by increasing the pressure on the solvent system. In FIG. 3, a tunable solvent is signified by 310 and a heteroatom-bicarbonate ion complex is signified by 320. In the mechanism shown in FIG. 3, $H_2CO_3^*$ (aq), $H^+$ (aq), and $HCO_3^-$ (aq) constitute the tunable solvent. In addition, the solubility of carbon dioxide in water increases as the temperature of the solvent system increases. However, formation of a complex between the $HCO_3^-$ and the dibenzothiophene also promotes the forward reaction to form $H_2CO_3^*$ (aq) in water, so that the concentration of $HCO_3^-$ (aq) may be maintained. Thus, equilibrium is established immediately after a complex forms through the disassociation of an equivalent of $H_2CO_3^*$ (aq) into $H^+$ (aq), and $HCO_3^-$ (aq). Accordingly, in embodiments, increasing the pressure in the contractor promotes the formation of the complex between one $HCO_3^-$ (aq) ion and one molecule of the organic heteroatom compound. Similarly, a decrease in pressure will drive the above mechanism in the opposite direction and will decrease the formation of complexes between ions and organic heteroatom compounds or may decompose any complexes that already exist in solution. Thus, it should be apparent that the organic heteroatom compound may be ejected from the solvent or may be made to aggregate or precipitate out of the solvent by decreasing the pressure.

The pressure in the contactor may vary according to the tunable solvent 150 that is used and the target organic heteroatom compounds, such as varying the pressure to produce more or less $HCO_3^-$ to attract various specific organic heteroatom compounds. However, in embodiments, the pressure in the contactor may be from about 2 bar to about 300 bar, such as from about 20 bar to 1 about 275 bar. In some embodiments, the pressure in the contractor may be from about 50 bar to about 250 bar, such as from about 75 bar to about 225 bar. In yet other embodiments, the pressure in the contactor may be from about 100 bar to about 200 bar. In still other embodiments, the pressure in the contractor may be from about 125 bar to about 175 bar, such as about 150 bar. It should be understood that the above ranges are intended to include each point between the disclosed endpoints, and that each pressure point between 2 bar and 300 bar is envisioned in this disclosure.

The temperature in the contactor may vary according to the tunable solvent 150 that is used and the target organic heteroatom compounds. In embodiments in which carbon dioxide is the tunable solvent, the temperature in the contactor may be greater than or equal to the critical temperature of carbon dioxide, such as about 20° C. greater than the critical temperature of carbon dioxide. In some embodiments, the temperature in the contactor is greater than or equal 40° C. above the critical temperature of carbon dioxide, such as about 60° C. greater than the critical temperature of carbon dioxide. In embodiments, the temperature in the contactor may be less than or equal to about 100° C., such as less than or equal to about 80° C.

Referring again to FIG. 1, in embodiments, the lean hydrocarbon 132 that has been extracted from the middle of the contactor 110 is sent to a recovery vessel 160 where the lean hydrocarbon 132 may be depressurized, causing a discharge stream 161 of any residual carbon dioxide and/or water to be separated from the lean hydrocarbon 132 and removed from the recovery vessel 160. The discharge stream 161 may be further treated to separate the carbon dioxide and water, which may be returned to the carbon dioxide storage unit 120 and the water storage unit 140, respectively. In other embodiments, the discharge stream may be discarded.

In embodiments, the solute rich tunable solvent 151, which may be extracted from the bottom of the contactor 110, may be fed to another vessel 170 where it is depressurized to tune down the ionic properties of the solute rich solvent 151 and thereby eject the solute 171, such as, for example, organic heteroatom compounds. The ejected solute 171 may then be stored and used in some other capacity. In some embodiments, the ejected solute 171 may be filtered out of the solute rich solvent 151. In other embodiments, the ejected solute 171 may be removed from the solute rich solvent 151 by aromatic solvent extraction. In either embodiment (i.e., whether the solute is removed by filtering or aromatic extraction), carbon dioxide 123, which has been released by lowering the pressure of the solute-rich solvent 151, is re-pressurized and returned to the carbon dioxide storage unit 120 where it may be dispersed with water 141 into the contactor, or premixed with the hydrocarbon 131.

In embodiments where aromatic solvent extraction is used to separate the solute 171 from the solute rich solvent 151, the solute rich aromatic solvent may be sent to an additional vessel where the aromatic solvent is evaporated off, such as by heating to the boiling point of the aromatic solvent, thus ejecting the solute 171. The evaporated aromatic solvent may then be condensed and reused to extract further solute 171 from a solute rich solvent 151, and the solute 171 may be stored and used in another capacity.

It should be understood that while FIG. 1 shows only one contactor 110, in embodiments, multiple contactors may be used in series depending on the number and characteristics of the organic heteroatom compounds to be removed. For example, the tunable solvent in a first contractor may be tuned to separate a first organic heteroatom compound, and a second contactor may be used to tune a second tunable solvent to separate a second organic heteroatom compound, such as, for example, having a pressure in the second contactor that is different from the pressure in the first contactor. Similarly, although FIG. 1 shows only one recovery vessel 160 for ejecting a solute 171 from a solute rich solvent 151, multiple vessels for ejected solute may be used. For example, where the solute rich solvent 151 includes multiple solutes with differing boiling points, multiple vessels may be used to eject the multiple solutes from the solute rich solvent 151.

Electric Field Assisted Mass Transfer

Figure 4:
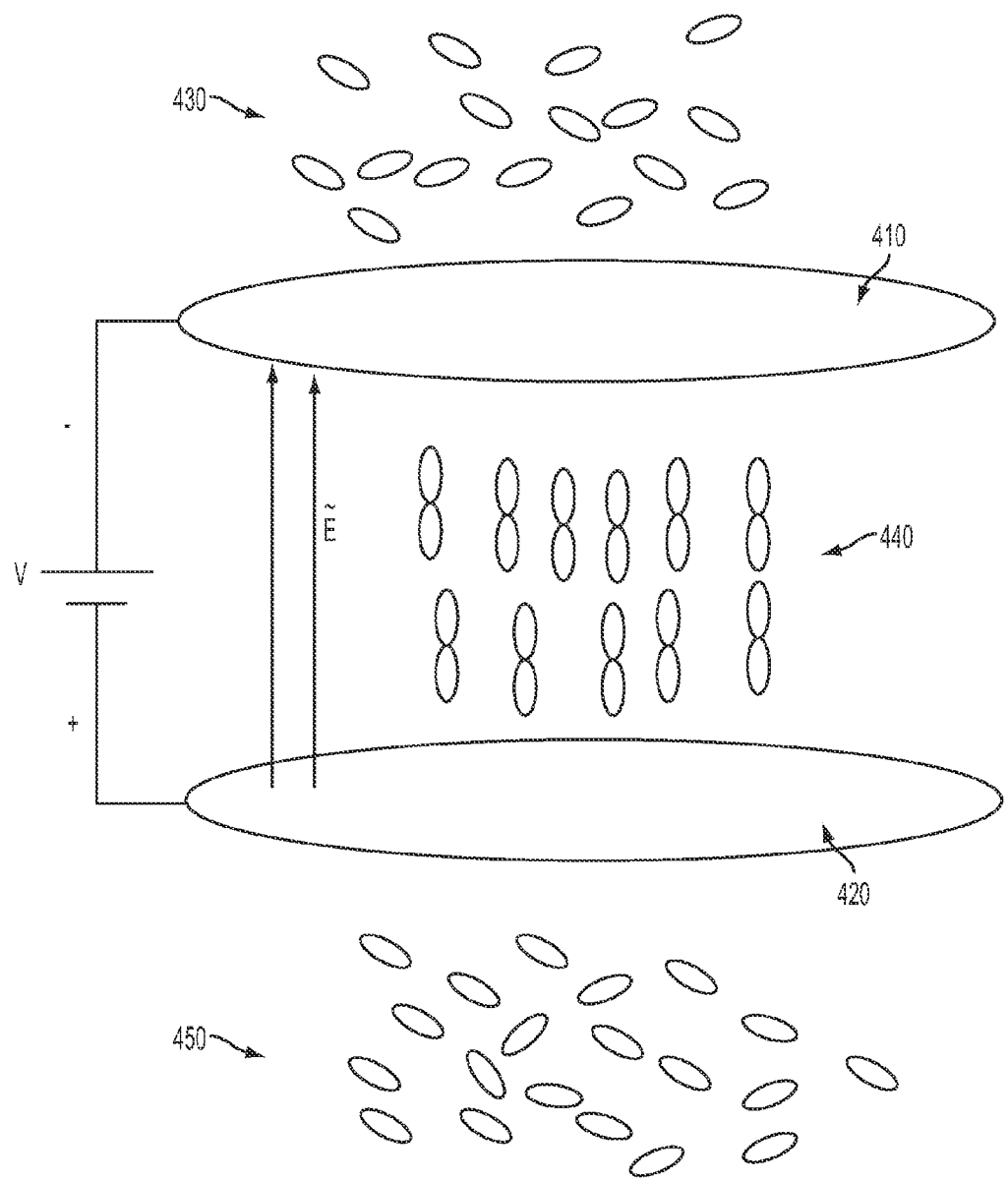
FIG. 4 schematically depicts electrical plates for aligning particles according to embodiments described herein.

Separation of organic heteroatom compounds from a hydrocarbon feedstock may be further enhanced using an electrical field. Referring to FIG. 4, in some embodiments, an electric field may be generated between two electrical plates 410 and 420 of a capacitor. This electric field may lead to alignment of ionic species within the electric field, thereby improving mass transfer between the ions. Particles 430 may be bipolar aqueous solvent particles, which are not aligned outside of the electric plates 410 and 420. Particles 450 may be organic bipolar particles that are not aligned outside of the electric plates 410 and 420. Between the electric plates may be heteroatom complexes, such as, for example, the complexes of tunable solvent and an organic heteroatom compound described above, that are aligned 440. The residence time and contact between the tunable solvent and the hydrocarbon feedstock may be increased by having the ions aligned within the electric plates 410 and 420. Further, using an electric field to align particles allows the tunable solvent to have a higher affinity toward the organic heteroatom compounds, and may facilitate mass transfer between the two plates by attracting polar ions.

In embodiments, the electrical plates may cause an alignment of organic heteroatom compounds from the hydrocarbon feedstock with respect to the electrical field and, thereby, facilitate their transfer toward the tunable solvent, where they are attracted into the aqueous phase of the solvent via the mechanisms discussed hereinabove. The outgoing tunable solvent, which is saturated with organic heteroatom compounds, may then be sent to a separate vessel where the organic heteroatom compounds may be removed from the tunable solvent by aromatic extraction of by reducing the pressure of the solvent system to allow the tunable solvent to eject the solute where the solute may be collected by, for example, filtration. After separation, the tunable solvent may be re-pressurized and returned to the contactor, and the organic heteroatom compound solutes may be stored and used in another capacity.

In embodiments, the electrical plates 410 and 420 may have through-holes to facilitate transfer of particles between the plates. In some embodiments, a bank of electrical plates may be used to form baffles or packing material within a contactor, such as contactor 110. The bank of plates may be offset from one another.

Thus, various embodiments of methods for recovering organic heteroatom compounds from a hydrocarbon feedstock have been described. In the methods, an aqueous solvent system such as an ionic liquid formed from pressurized carbon dioxide and water, may be contacted with a hydrocarbon feedstock such as crude oil or a crude oil fraction. The contacting may occur in a contactor vessel at a pressure and temperature that tunes the aqueous solvent system to selectively form complexes with organic heteroatom compounds in the hydrocarbon feedstock. The complexes may then be transferred to a recovery vessel, in which pressure, temperature, or both, may be adjusted to cause the organic heteroatom compounds to come out of solution. Thereby, the organic heteroatom compounds may be used for further applications. Unlike with common denitrogenation or desulfurization processes used for hydrocarbon feedstocks such as crude oil, the organic heteroatom compounds maintain their chemical structure and can be utilized as a valuable byproduct of petroleum refining that previously would have been wasted.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A method for reducing or removing one or more organic heteroatom compounds from a hydrocarbon feedstock to form a lean hydrocarbon, the method comprising:
feeding a hydrocarbon feedstock into a contactor, the hydrocarbon feedstock comprising at least one hydrocarbon and at least one organic heteroatom compound, the at least one organic heteroatom compound chosen from nitrogen-containing heterocyclic compounds, sulfur-containing heterocyclic compounds, porphyrins, organometallic compounds, and combinations thereof;

feeding an aqueous solvent into the contactor to form an extraction mixture of the aqueous solvent with the hydrocarbon feedstock, the aqueous solvent comprising an ionic liquid formed from pressurized carbon dioxide and water;

establishing a contactor pressure and a contactor temperature of the extraction mixture in the contactor that together tune the aqueous solvent to selectively form a mixture containing a lean hydrocarbon and a solvent complex with the at least one organic heteroatom compound, wherein the contactor temperature is from greater than the critical temperature of carbon dioxide to about 100° C.;

extracting the solvent complex to a recovery vessel from the extraction mixture in the contactor; and recovering the lean hydrocarbon from the contactor.

2. The method of claim 1, further comprising recovering the at least one organic heteroatom compound from the solvent complex.

3. The method of claim 2, wherein the organic heteroatom compound is recovered from the solvent complex by adjusting a recovery temperature of the recovery vessel, a recovery pressure of the recovery vessel, or both, to decompose the solvent complex in the recovery vessel into carbon dioxide and the at least one organic heteroatom compound, the method further comprising recovering the at least one organic heteroatom compound from the recovery vessel.

4. The method of claim 3, wherein adjusting the recovery temperature of the recovery vessel, the recovery pressure of the recovery vessel, or both, comprises reducing the recovery pressure to less than the contactor pressure.

5. The method of claim 3, wherein adjusting the recovery temperature of the recovery vessel, the recovery pressure of the recovery vessel, or both, comprises lowering the recovery temperature to less than the contactor temperature.

6. The method of claim 1, wherein the hydrocarbon feedstock comprises crude oil or a crude oil fraction.

7. The method of claim 1, wherein the at least one organic heteroatom compound is selected from the group consisting of pyrrole, pyridine, quinoline, carbazole, indole, nickel-tetraphenyl-porphyrin, vanadyl-tetraphenyl-porphyrin, thiophene, benzothiophene, dibenzothiophene, and 7,8,9,10-tetrahydro-benzo[b]naphtho[2,3-d]thiophene, and combinations thereof.

8. The method of claim 1, wherein the contactor pressure is from about 2 bar to about 300 bar.

9. The method of claim 8, wherein the contactor pressure is greater than or equal to the critical pressure of $CO_2$.

10. The method of claim 1, wherein recovering the at least one organic heteroatom compound comprises mixing an aromatic solvent with the solvent complex.

11. The method of claim 1, wherein:
feeding the hydrocarbon feedstock comprises spraying the hydrocarbon feedstock into a bottom of the contactor; and
feeding the aqueous solvent comprises spraying the aqueous solvent into a top of the contactor.

12. The method of claim 11, wherein the density of the aqueous solvent is greater than the density of the hydrocarbon feedstock, whereby the extraction mixture phase separates into at least an organic phase and an aqueous phase and at least a portion of the solvent complex migrates into the aqueous phase.

13. The method of claim 12, wherein extracting the solvent complex comprises removing the at least a portion of the solvent complex from the aqueous phase or from a $CO_2$ phase that forms above the aqueous phase in the contactor.

14. The method of claim 1, further comprising mixing the hydrocarbon feedstock with supercritical $CO_2$ before feeding the hydrocarbon feedstock into the contactor.

15. The method of claim 1, further comprising reducing or removing at least one additional organic heteroatom compounds in at least one additional contactor in series with the contactor, wherein in each additional contactor a contactor pressure and a contactor pressure are established that together tune an aqueous solvent to selectively form a solvent complex with at least one organic heteroatom compound remaining in a lean hydrocarbon fed into the additional contactor.

16. The method of claim 1, wherein the lean hydrocarbon comprises at least one second organic heteroatom compound not extracted from the hydrocarbon stream in the contactor, the method further comprising:
feeding the lean hydrocarbon into a second contactor;
feeding a second aqueous solvent into the second contactor to form a second extraction mixture of the second aqueous solvent with the lean hydrocarbon, the second aqueous solvent comprising an ionic liquid formed from pressurized carbon dioxide and water;
establishing a second contactor pressure and a second contactor temperature of the second extraction mixture in the second contactor that together tune the second aqueous solvent to selectively form a mixture containing a second lean hydrocarbon and a second solvent complex with the at least one second organic heteroatom compound;
extracting the second solvent complex to a second recovery vessel from the second extraction mixture in the second contactor; and
recovering the second lean hydrocarbon from the second contactor.

17. The method of claim 1, wherein the at least one organic heteroatom compound comprises a nitrogen-containing heterocyclic compound.

18. The method of claim 17, wherein:
the hydrocarbon feedstock is crude oil or a crude fraction; and
the nitrogen-containing heterocyclic compound is chosen from pyrrole, pyridine, quinoline, carbazole, indole, and combinations thereof.

19. The method of claim 1, wherein the at least one organic heteroatom compound comprises a sulfur-containing heterocyclic compound.

20. The method of claim 19, wherein:
the hydrocarbon feedstock is crude oil or a crude fraction; and
the sulfur-containing heterocyclic compound is chosen from thiophene, benzothiophene, dibenzothiophene, and 7,8,9,10-tetrahydro-benzo[b]naphtho[2,3-d]thiophene, and combinations thereof.

21. The method of claim 1, wherein the at least one organic heteroatom compound comprises an organometallic compound.

22. The method of claim 21, wherein the organometallic compound is a porphyrin.

23. The method of claim 22, wherein:
the hydrocarbon feedstock is crude oil or a crude fraction; and
the porphyrin is chosen from nickel-tetraphenyl-porphyrin, vanadyl-tetraphenyl-porphyrin, and combinations thereof.

24. The method of claim 1, wherein the contactor comprises electrical plates, the method further comprising activating the electrical plates to align ions of the ionic liquid and ions of the at least one organic heteroatom compound.

25. The method of claim 1, wherein the contactor is a packed bed contactor, a fluidized bed contactor, or a baffled contactor.

26. The method of claim 1, wherein:
the density of the aqueous solvent is greater than the density of the hydrocarbon feedstock; and
the hydrocarbon feedstock is fed by spraying into a top portion of the contactor; and
the aqueous solvent is fed by spraying into a bottom portion of the contactor.

27. The method of claim 1, wherein:
the density of the hydrocarbon feedstock is greater than the density of the aqueous solvent; and
the hydrocarbon feedstock is fed by spraying into a bottom portion of the contactor; and
the aqueous solvent is fed by spraying into a top portion of the contactor.

28. The method of claim 1, wherein:
the mixture containing the lean hydrocarbon and the solvent complex separates into four phase regions after the contactor pressure and the contactor temperature of the extraction mixture are established, the four phase regions comprising:
a first phase containing supercritical and subcritical carbon dioxide;
a second phase region below the first phase region and containing lean hydrocarbon and carbon dioxide;
a third phase region below the second phase region and containing aqueous carbon dioxide, water, hydrogen ions, carbonic acid, hydrocarbon, and supercritical carbon dioxide; and
a fourth phase region below the third phase region and containing aqueous carbon dioxide, hydrogen ions, water, carbonic acid, and solute-rich solvent;
the solvent complex is extracted from the fourth phase region; and
the lean hydrocarbon is recovered from the second phase region.

* * * * *